United States Patent [19]

Weeks

[11] Patent Number: Plant 7,264

[45] Date of Patent: Jul. 10, 1990

[54] ROSE PLANT NAMED 'VEROLWEK'

[75] Inventor: O. L. Weeks, 12610 Central Ave., Ste. 76, Chino, Calif. 91710

[73] Assignee: O. L. Weeks, Chino, Calif.

[21] Appl. No.: 304,490

[22] Filed: Jan. 31, 1989

[51] Int. Cl.[5] ..... A01H 5/00

[52] U.S. Cl. ..... Plt./15

[58] Field of Search ..... Plt. 15

[56] References Cited

U.S. PATENT DOCUMENTS

P.P. 6,95 6/1946 Shelly ..... Plt. 18

OTHER PUBLICATIONS

Meikle, C. E. (Ed.), *Modern Roses* 8, The McFarland Co., Harrisburg, Pa., 1980, p. 68.

A.R.S. American Rose Registry, 1988, Pub. American Rose Society, 1988, p. 44.

*Primary Examiner*—James R. Feyrer

*Attorney, Agent, or Firm*—Christie, Parker & Hale

[57] ABSTRACT

A new hybrid tea rose variety with relatively large blooms of yellow coloring.

1 Drawing Sheet

SUMMARY OF THE INVENTION

The present invention relates to a new and distinct variety of rose plant of the hybrid tea rose class, which was originated by my crossing as seed parent an unnamed, unpatented rose of my creation and as pollen parent the rose known as "Yellow Yo Yo". The varietal denomination of this new rose is "Verolwek".

Among the novel characteristics possessed by this new variety which distinguishes it from its parent and all other varieties of which I am aware are its attractive relatively large yellow flowers of good form that maintain their color through development and aging.

The new variety, "Verolwek", produces full, vigorous, heavily foliaged plants and masses of medium to deep yellow, large blooms. The flowers are somewhat informal in form as compared to the classic exhibition rose. However, the petals are large and maintain good substance through aging. The flowers hold well upon opening and their disciplined form is one of the charms of this new rose cultivar.

"Celebrity" is a dual purpose variety. The robust plant with full beautiful foliage covered recurrently with masses of large distinctive yellow flowers is useful as a desirable landscape rose and also produces an abundance of long stem flowers useful for cutting.

Asexual reproduction by budding of the new variety as performed in Kern County, Calif. shows that the foregoing and other distinguishing characteristics come true to form and are established and transmitted through succeeding propagations.

BRIEF DESCRIPTION OF DRAWING

The accompanying drawing shows typical specimens of the vegetative growth and flowers of the new variety in different stages of development and as depicted in color as nearly true as it is reasonably possible to make the same in a color illustration of this character.

HORTICULTURAL DESCRIPTION OF THE NEW VARIETY

The following is detailed description of my new variety, with color terminology in accordance with The Royal Horticultural Society Colour Chart (R.H.S.C.C.). The terminology used in color description herein refers to plate numbers in the aforementioned color chart, e.g., "151C" is plate 151C of The Royal Horticultural Society Colour Chart.

Parentage: Seedling.

*Seed parent.*—Unnamed, unpatented seedling.

*Pollen parent.*—Yellow Yo Yo.

Class: Hybrid Tea.

The following observations are made of specimens grown outdoors in Kern County, Calif., during the month of October.

1. FLOWER

Blooming habit: Recurrent.

A. Bud:

(1) *Size.*—Large.

(2) *Form.*—Short, ovoid.

(3) *Color.*—After sepals fall, near 12B to 12C with occasional narrow central flush or reddish orange.

(4) *Sepals.*—Longer than bud, some simple and some foliated.

(5) *Peduncle.*—Length — long. Aspect — straight. Strength — erect, heavy, strong. Color — near 146C with greyed red overlay, near 178A.

B. Bloom:

(1) *Size.*—Average size when fully expanded — about 5 to 5½ inches.

(2) *Borne.*—Singly and several together in small sprays.

(3) *Form.*—High centered at first, petals loosely rolled outward, flower maintains form throughout, opens well.

(4) *Petalage.*—Number of petals under normal conditions — about 30 to 35.

(5) Color.—After sepals fall and as flower opens, color appears as near 11A to 12A and near 12A at the base of the petals. Petal undersurface is also near 12A. As blooms age, color lightens to near 12C to D. General tonality at a distance is attractive yellow.

C. Petals:

(1) *Texture.*—Thick, heavy.

(2) *Appearance.*—Inside — satiny, outside — satiny.

(3) *Form.*—Acuminate.

(4) *Arrangement.*—Regularly arranged, imbricated.
(5) *Petaloids in center.*—Many.
(6) *Persistence.*—Drop off cleanly.
(7) *Fragrance.*—None.
(8) *Lasting quality.*—Long on plant and as cut flower.

2. REPRODUCTIVE ORGANS

A. Stamens, filaments and anthers:
(1) *Arrangement.*—Irregularly arranged around styles.
(2) *Color.*—Stamens bright yellow, anthers yellow.
B. Pollen:
*Color.*—Medium yellow.
C. Styles: Uneven length, bunched.
D. Stigmas:
*Color.*—Reddish tipped deep yellow.
E. Hips: None observed.

3. PLANT

A. Form: Tall, upright.
B. Growth: Very Vigorous.
*Height attained.*—about 6 feet.
C. Foliage: Mostly Compound 5 leaflets.
(1) *Size.*—Medium to large.
(2) *Quantity.*—Abundant.
(3) *Color.*—New foliage: Upper side — yellow-green, near 152A to B Under side — yellow-green, near 152A to B Old foliage: Upper side — near 147A Under side — near 147B to C.
(4) *Shape.*—Oval, pointed.
(5) *Texture.*—Upper side is leathery, semi glossy and under side is dull.
(6) *Edge.*—Serrated.
(7) *Serration.*—Finely Serrate.
(8) *Leaf stem.*—Color — pale green with reddish overlay.
(9) *Stipules.*—Long, finely bearded on the edges.
(10) *Resistance to disease.*—Mildew — Average.
D. Wood:
(1) *New wood.*—Color — light green, near 146C with reddish overlay. Bark — smooth.
(2) *Old wood.*—Color — near 147B. Bark — smooth.
E. Thorns:
(1) *Thorns.*—Quantity (main stalk) — few. On laterals from stalk — normally few, sometimes more. Form — narrow, flat base. Length — medium. Color — reddish green. Position — irregular.
(2) *Prickles.*—Few to none.
F. Winter hardiness: Average.

I claim:

1. A new and distinct variety of rose plant of the hybrid tea rose class, substantially as shown and described, characterized particularly by relatively large, attractive, yellow flowers.

* * * * *

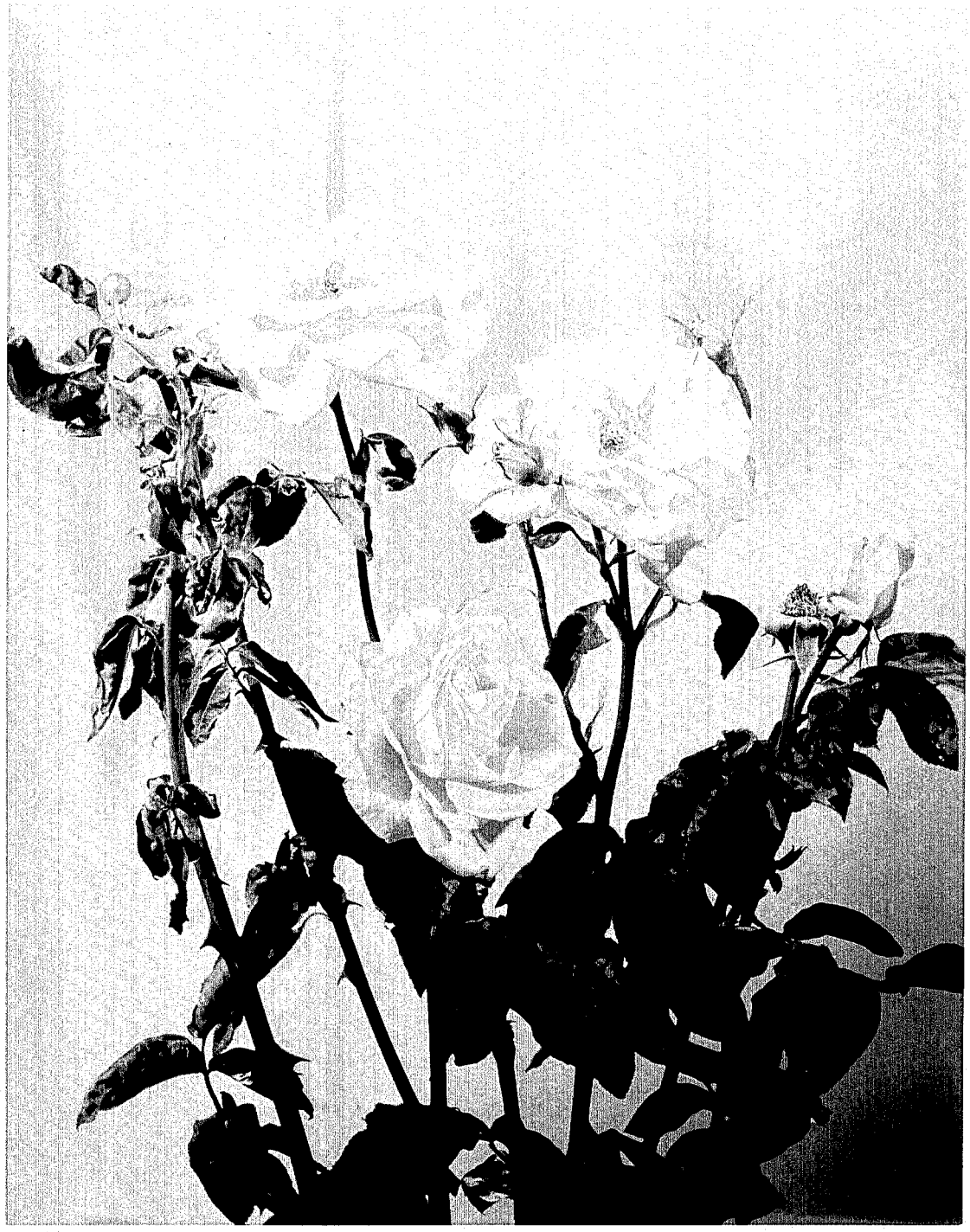

UNITED STATES PATENT AND TRADEMARK OFFICE

CERTIFICATE OF CORRECTION

PATENT NO. : Plant 7,264

DATED : July 10, 1990

INVENTOR(S) : O. L. Weeks

It is certified that error appears in the above-identified patent and that said Letters Patent is hereby corrected as shown below:

On the title page:

[73] Assignee: Delete "O. L. Weeks, Chino, Calif."

Column 1, line 10, change "parent" to -- parents --.

Column 1, line 22, change "'Celebrity'" to -- "Verolwek" --.

Column 1, line 41, before "detailed" insert -- a --.

Column 3, line 30, after "B" insert a semicolon.

Column 4, line 2, after "A" insert a semicolon.

Signed and Sealed this

Seventh Day of April, 1992

*Attest:*

*Attesting Officer*

HARRY F. MANBECK, JR.

*Commissioner of Patents and Trademarks*